United States Patent
Kujawski et al.

(10) Patent No.: US 7,309,461 B2
(45) Date of Patent: Dec. 18, 2007

(54) ULTRASONIC CRIMPING OF A VARIED DIAMETER VASCULAR GRAFT

(75) Inventors: Dennis Kujawski, Warwick, NY (US); Matthew Hain, Wayne, NJ (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 412 days.

(21) Appl. No.: 10/822,955

(22) Filed: Apr. 12, 2004

(65) Prior Publication Data

US 2005/0228489 A1    Oct. 13, 2005

(51) Int. Cl.
  *B06B 1/02*  (2006.01)
  *B29C 59/00* (2006.01)
  *A61F 2/06*  (2006.01)

(52) U.S. Cl. ............... 264/443; 264/442; 264/506; 623/1.28; 623/1.3

(58) Field of Classification Search ............ None
See application file for complete search history.

(56) References Cited

U.S. PATENT DOCUMENTS

| | | | |
|---|---|---|---|
| 3,230,598 A * | 1/1966 | Rosenstein et al. ......... 28/268 |
| 3,317,924 A * | 5/1967 | Le Veen et al. .......... 623/1.54 |
| 3,635,609 A * | 1/1972 | Balamuth .................. 425/3 |
| 4,028,033 A * | 6/1977 | Bryant .................... 425/183 |
| 4,512,761 A * | 4/1985 | Raible ..................... 604/8 |
| 4,517,687 A   | 5/1985 | Liebig et al. |
| 4,647,416 A   | 3/1987 | Seiler, Jr. et al. |
| 4,957,669 A   | 9/1990 | Primm |
| 5,026,513 A   | 6/1991 | House et al. |
| 5,128,092 A   | 7/1992 | Asaumi et al. |
| 5,139,515 A   | 8/1992 | Robicsek |
| 5,178,630 A   | 1/1993 | Schmitt |
| 5,178,634 A   | 1/1993 | Ramos Martinez |
| 5,314,468 A   | 5/1994 | Ramos Martinez |
| 5,387,235 A * | 2/1995 | Chuter ................... 623/1.11 |
| 5,641,373 A   | 6/1997 | Shannon et al. |
| 5,746,856 A   | 5/1998 | Hendershot et al. |
| 5,800,514 A   | 9/1998 | Nunez et al. |
| 5,814,390 A * | 9/1998 | Stokes et al. .............. 428/181 |
| 5,843,173 A   | 12/1998 | Shannon et al. |
| 5,861,026 A   | 1/1999 | Harris et al. |
| 5,891,195 A   | 4/1999 | Klostermeyer et al. |
| 5,910,168 A   | 6/1999 | Myers et al. |

(Continued)

FOREIGN PATENT DOCUMENTS

JP    58131036    8/1993

OTHER PUBLICATIONS

Dukane Corporation Ultrasonic Division, Ultrasonic Processing of Fabric and Films, Dec. 2003, pp. 1-4.*

*Primary Examiner*—Christina Johnson
*Assistant Examiner*—Jeff Wollschlager
(74) *Attorney, Agent, or Firm*—Hoffmann & Baron, LLP

(57) ABSTRACT

A method of crimping a varied diameter graft is includes the steps of (i) providing a flat-woven tubular graft having an enlarged woven bulbous portion disposed between flat-woven tubular ends, wherein the flat-woven diameter of the bulbous section is greater than the flat woven diameters of the tubular ends; (ii) providing a mandrel shaped and sized to the woven bulbous section and having a curved crimping surface; and (iii) positioning the curved crimping surface within the bulbous woven section so that the bulbous woven section contours to the curved crimping surface.

13 Claims, 3 Drawing Sheets

U.S. PATENT DOCUMENTS

| | | | |
|---|---|---|---|
| 6,039,755 A | 3/2000 | Edwin et al. | |
| 6,054,002 A | 4/2000 | Griesbach, III et al. | |
| 6,090,137 A * | 7/2000 | Schmitt | 623/1.44 |
| 6,187,033 B1 * | 2/2001 | Schmitt et al. | 623/1.35 |
| 6,190,590 B1 | 2/2001 | Randall et al. | |
| 6,203,735 B1 | 3/2001 | Edwin et al. | |
| 6,295,714 B1 | 10/2001 | Roychowdhury et al. | |
| 6,342,070 B1 | 1/2002 | Nguyen-Thien-Nhon | |
| 6,347,632 B1 | 2/2002 | Eberhardt et al. | |
| 6,352,554 B2 | 3/2002 | DePaulis | |
| 6,454,989 B1 | 9/2002 | Neely et al. | |
| 6,461,382 B1 | 10/2002 | Cao | |
| 6,544,285 B1 | 4/2003 | Thubrikar et al. | |
| 6,547,820 B1 * | 4/2003 | Staudenmeier | 623/1.49 |
| 6,605,119 B1 | 8/2003 | Colone et al. | |
| 6,635,214 B2 | 10/2003 | Rapacki et al. | |
| 6,652,574 B1 | 11/2003 | Jayaraman | |
| 6,746,480 B2 * | 6/2004 | Scholz et al. | 623/1.31 |
| 2002/0036220 A1 * | 3/2002 | Gabbay | 224/191 |
| 2003/0078650 A1 * | 4/2003 | Nunez et al. | 623/1.51 |
| 2003/0109919 A1 * | 6/2003 | Gantt et al. | 623/1.35 |
| 2003/0196717 A1 | 10/2003 | Nunez et al. | |
| 2004/0019375 A1 * | 1/2004 | Casey et al. | 623/1.28 |
| 2004/0049264 A1 | 3/2004 | Sowinski et al. | |

* cited by examiner

ULTRASONIC CRIMPING OF A VARIED DIAMETER VASCULAR GRAFT

FIELD OF THE INVENTION

The present invention relates to ultrasonic crimping of a varied diameter vascular graft, such as an aortic root vascular graft.

BACKGROUND OF THE INVENTION

Tubular woven fabrics have been used for soft-tissue implantable prostheses to replace or repair damaged or diseased lumens in the body. In particular, endoprostheses are used in the vascular system to prevent the blood from rupturing a weakened section of the vessel. Such endoluminal conduits are generally affixed in a specified location in the vessel by means of stents, hooks or other mechanisms which serve to secure the device in place. Endoluminal tubular devices or conduits can also be used in other lumens in the body, such as in the esophagus and colon areas.

Weaving is commonly employed to fabricate various tubular shaped products. For example, implantable tubular prostheses which serve as conduits, such as vascular grafts, esophageal grafts and the like, are commonly manufactured using tubular weaving techniques, wherein the tubular product is woven as a flat tube. In such weaving processes, a variety of yarns are interwoven to create the tubular fabric. For example, a set of warp yarns is used which represents the width of the product being woven, and a fill yarn is woven between the warp yarns. The fill yarn is woven along the length of the warp yarns, with each successive pass of the fill yarn across the warp yarns for each side of the tube representing one machine pick. Thus, two machine picks represent one filling pick in a tubular woven structure, since weaving one fill yarn along the entire circumference of the tube, i.e., one filling pick, requires two picks of the weaving machine. As such, in a conventional woven product, the fill yarn is woven along the length of the warp yarns for a multiple number of machine picks, with the woven product produced defined in length by the number of filling picks of the fill yarn and defined in width by the number of warp yarns in which the fill yarn is woven therebetween.

Some damaged or diseased lumens, however, have quite complex shapes. For example, the root portion of the aorta is provided sinuses or bulges that surround the aortic valve, which are called the sinuses of Valsalva. The diameter and orifice area of the aortic root are greater at the vicinity of the sinuses as compared to other portions of the root. With such a complex geometry, implantable grafts matching such complexity have often been made by suturing differently shaped graft components together. For example, U.S. Pat. No. 6,352,554 to DePaulis describes a method for forming a graft for the aortic root by suturing a bulbous woven section in between two straight tubular woven sections. Further, the bulbous woven section is also formed cutting or otherwise attaching woven materials. Still further, the various woven portions are crimped prior to suturing the sections together. Such techniques are not only costly as numerous textile portions must be sutured to one and the other, but also serve as a potential source for leakage as it is difficult to suture fluid-tight seams among the textile components.

The present invention provides for a seamlessly woven complex grafts including seamlessly woven projections or petals, such as but not limited to aortic root grafts, and methods for producing the same.

SUMMARY OF THE INVENTION

In one aspect of the present invention a method of crimping a varied diameter graft is provided. The method includes the steps of (i) providing a flat-woven tubular graft having an enlarged woven bulbous portion disposed between flat-woven tubular ends, wherein the flat-woven diameter of the bulbous section is greater than the flat woven diameters of the tubular ends; (ii) providing a mandrel shaped and sized to the woven bulbous section and having a curved crimping surface; and (iii) positioning the curved crimping surface within the bulbous woven section so that the bulbous woven section contours to the curved crimping surface.

The method of the present invention further includes the step of heating the bulbous woven portion to set the shape of the bulbous woven portion. Alternatively, the method of the present invention may further include the step of applying heat and pressure to the bulbous woven portion to set the shape of the bulbous woven portion. Desirably, the heating is caused by ultrasonic action.

The method of the present invention may further include the steps of (i) providing a horn having a crimped surface mateable to the crimped surface of the mandrel; (ii) aligning the crimping surfaces of the horn over the bulbous woven section; (iii) securing the woven section between the crimping surfaces of the horn and the mandrel; and (iv) causing the woven portion to heat by ultrasonic action to heat set crimps thereat. The steps may be repeated until the graft is circumferentially crimped.

Further, the method of the present invention may include the steps of (i) providing a rotatable horn having a crimped surface mateable to the crimped surface of the rotatable mandrel made to rotate; (ii) aligning the crimping surfaces of the rotatable horn over the bulbous woven section; (iii) securing the woven section between the crimping surfaces of the rotatable horn and the rotatable mandrel; and (iv) causing the woven portion to heat by ultrasonic action to heat set crimps thereat.

In another aspect of the present invention, a method of crimping a varied diameter graft is provided. The method includes the steps of (i) providing a flat-woven tubular graft having an enlarged woven bulbous portion disposed between flat-woven tubular ends, wherein the flat-woven diameter of the bulbous section is greater than the flat woven diameters of the tubular ends; (ii) providing a tubular cylindrical mandrel having a diameter such that its exterior surface is slidable engageable within the woven tubular ends; (iii) providing a bulbously shaped mandrel donut, the donut being slidable over the cylindrical mandrel, the donut having a crimped exterior surface; (iv) aligning the donut within the bulbous woven section of the graft; (v) sliding the cylindrical mandrel through the donut; (vi) crimping the graft over the cylindrical mandrel and bulbous donut; and (viii) removing the cylindrical mandrel and the bulbous donut from the graft. The removing step may further include the steps of (i) slidingly removing the cylindrical mandrel from the graft and the bulbous donut; and (ii) removing the donut from the graft. The tubular mandrel may include a crimping surface, and the flat-woven tubular ends may be crimped over the crimping surface of the mandrel. The removing step may further include the step of compressing the donut, collapsing the donut, disassembling the donut, and combinations thereof In another aspect of the present invention, a system for crimping a varied diameter graft is provided. The system includes (i) a mandrel having a bulbous portion, the bulbous portion having a curved crimping surface; and (ii) a horn having a curved crimped surface aligningly engageable to the curved crimping surface of the mandrel; and (iii) a source of ultrasonic energy.

In still another aspect of the present invention, a mandrel for crimping a varied diameter graft is provided. The mandrel includes a mandrel with a bulbous portion, the bulbous portion having a curved crimping surface.

In still further another aspect of the present invention, a mandrel for crimping a varied diameter graft is provided. The mandrel includes (i) a tubular mandrel having a diameter such that its exterior surface is slidably engageable within a vascular tubular graft, wherein the exterior mandrel surface has a crimping surface; and (ii) a bulbously shaped mandrel donut, wherein the donut is slidable engageable over the tubular mandrel, the donut having a curved exterior crimping surface. The donut may be collapsible, expandable, inflatable, and combinations thereof. Further, the donut may be made from a resilient material. Further, the donut may be made from multiple parts and may be disassembleable.

Alternatively, or in addition to ultrasonic action, heating of the graft may be caused by steam.

DETAILED DESCRIPTION OF THE PREFERRED EMBODIMENT

Ultrasonic welding or crimping may be accomplished through the use of a rapidly vibrating, usually 20, 30 or 40 KHz, of a part called a horn that impinges on the two or more pieces of the material to be welded or on one piece of material to be shaped or crimped with a set force. On the opposite side of the piece or pieces being welded is a solid fixture that provides support for the pieces called the anvil or mandrel. The rapid vibration of the horn on the piece or pieces held rigidly in place by the mandrel causes friction in and between the piece(s). The friction causes the material to soften, and the force of the horn's impingement causes the pieces to fuse or weld, or in the case of a single piece to crimp.

Tooling is one of several variables to consider when using ultrasonics. The shape of the horn and mandrel determines the shape of the finished part acted upon by ultrasonics. The tooling is generally designed to fit the particular application. An ultrasonic welder may be purchased from companies such as Branson Ultrasonic Corp., Danbury, Conn. and Dukane Corp., St. Charles, Ill. The frequency of an ultrasonic welder generally is fixed and runs at either 20, 30 or 40 kHz. The amplitude of the horn may be adjusted by the use of a metal part placed between the ultrasonic driver and horn called a booster. Parameters such as weld time and impingement force are adjusted to impart more or less energy onto the pieces to be welded to achieve the optimum weld.

Ultrasonic welding of polyester fabric is a useful means of crimping varied diameter grafts. As a general matter, if the welder energy is decreased sufficiently, softening of the polyester will decrease and the polyester may be shaped as opposed to welded. It is possible to cause the polyester to form a crimped shape using ultrasonics. Branson welder model 2000 IW runs at 20 kHz and is equipped with a 2.5 inch diameter air cylinder to control impingement force. It may be run at about from 100 milliseconds to about one second with the air pressure set to from about 10 psi to 100 psi to achieve a crimped polyester graft of about between 15 mm to about 30 mm diameter using a horn-mandrel combination that imparts a crimp in the graft.

Figure 1:
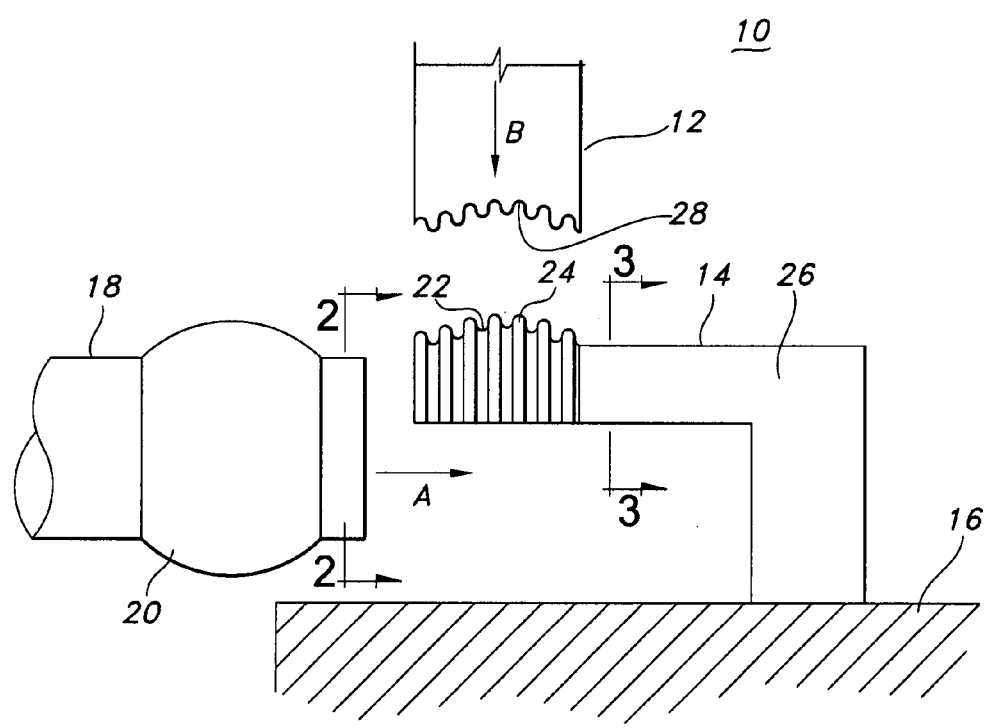
FIG. 1 is an illustration of an ultrasonic crimping system according to the present invention, including an ultrasonic horn and a mandrel for crimping a varied diameter graft.

A system 10 for ultrasonically crimping a varied diameter graft is depicted in FIG. 1. The system includes a horn 12, a mandrel 14 and a base 16, interrelated as shown. A varied diameter graft 18 may be placed over the mandrel 14. Desirably, the varied diameter graft is a seamlessly woven graft. One method for weaving such a varied diameter graft is described in U.S. patent application Ser. No. 10/823,456 titled "Varied Diameter Vascular Graft" and filed on Apr. 12, 2004, which published as US 2005/0228488 A1, the contents of which is incorporated herein by reference. Further, the varied diameter graft 18 may have a plurality of petal-like projections (not shown) associated with it bulbous portion 20. Details of such varied diameter grafts with petal-like projections is described in U.S. patent application Ser. No. 10/823,061 titled "Tri-Petaled Aortic Root Vascular Graft" and filed on April 12, 2004, which published as US 2005/0228487 A1, the contents of which is incorporated herein by reference.

Figure 2:
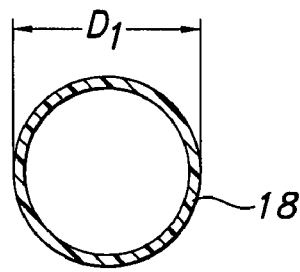
FIG. 2 is a cross-sectional view of the graft of FIG. 1 taken along the 2-2 axis.
Figure 3:
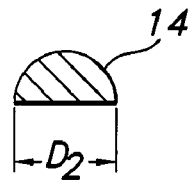
FIG. 3 is a cross-sectional view of the mandrel of FIG. 1 taken along the 3-3 axis.

As depicted in FIGS. 2 and 3, the diameter, $D_1$, of graft 18 is larger than the diameter, $D_2$, of mandrel 14. This permits graft 18 to be placed over the mandrel 14, as indicated by vector "A". Further as depicted in FIG. 3, the cross-sectional area of mandrel 14 need not be circular, but can be a truncated shape to allow for access within graft 18. Further, mandrel 14 has a crimping surface 22 disposed on a bulbous portion 24 which generally matches the contour of the bulbous portion 20 of graft 18. Other portions 26 of the mandrel 14 may also have a crimped surface (not shown) for crimping straight tubular portion of graft 18.

The horn 12 also contains a crimping surface 28 which is mateable to the crimping surface 22 of the mandrel 14. The horn contains a source of ultrasonic energy, depicted by Vector B, for crimping the graft. The horn 12 is placed over the graft 18 in a mating fashion to the mandrel 14. As described, the ultrasonic energy causes the graft material to take on the contours of the crimping surfaced 22 and 28. As the mandrel 14 is sized smaller than the graft 18, several applications of ultrasonic energy are necessary to complete the crimping around the entire circumference of the graft 18. After crimping one portion of the graft 18 between the horn 12 and the mandrel 14, the graft 18 may be rotated to crimp another portion. The process is continued until the radial or circumferential crimping is completed. Alternatively, the horn 12 and the mandrel 14 may be rotated to complete the crimping at the different portions of the graft 18.

Figure 5:
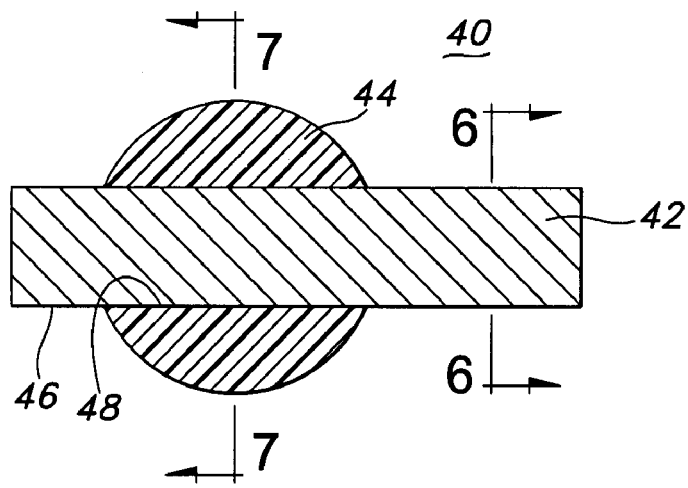
FIG. 5 is a cross-sectional view of the mandrel of FIG. 4 taken along the 5-5 axis.
Figure 4:
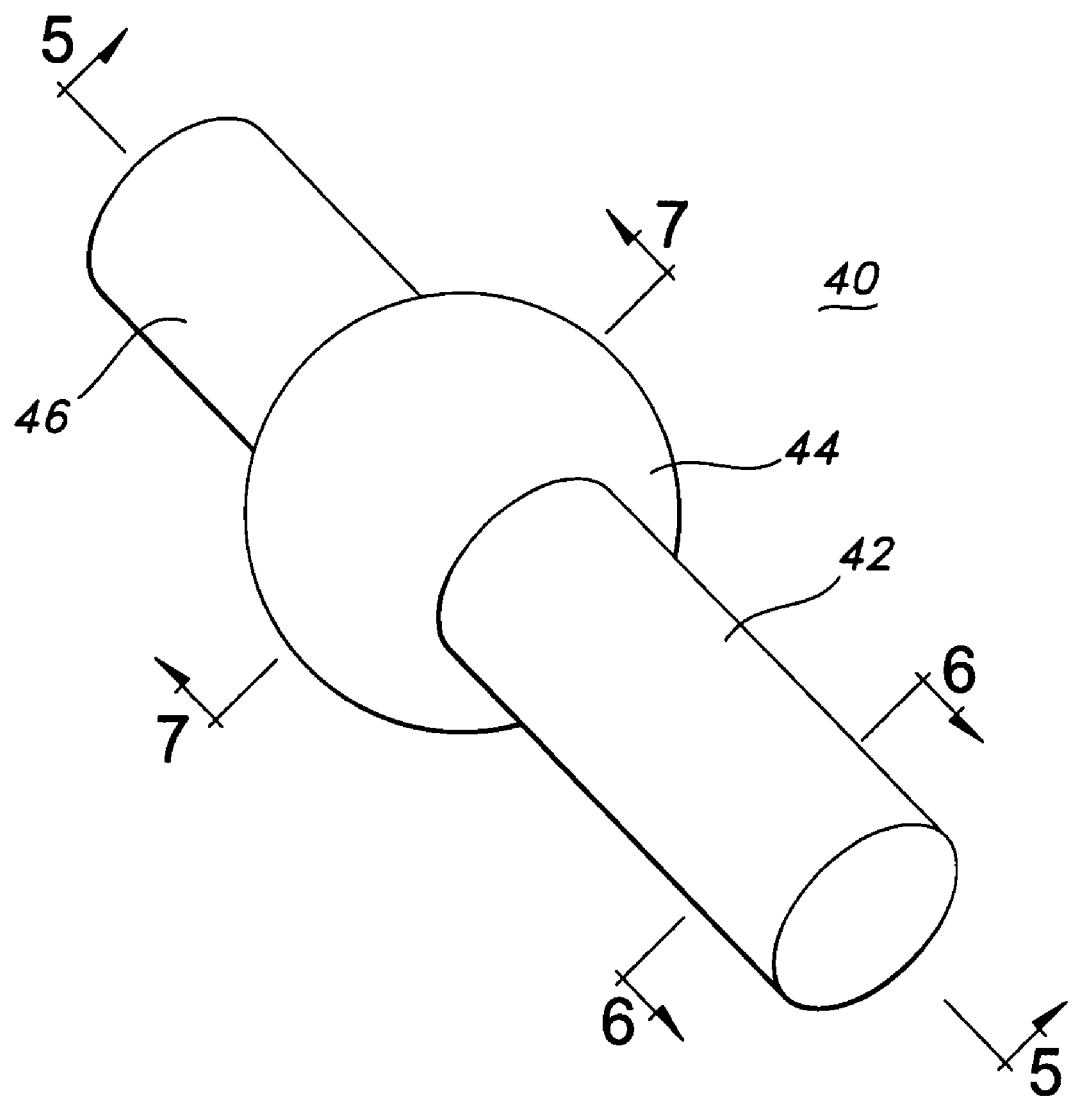
FIG. 4 is a perspective view of an alternate mandrel having a donut and a cylindrical member useful for crimping varied diameter grafts.

The present invention, however, is not limited to the use of system 10 for ultrasonically crimping varied diameters grafts. For example, other mandrel designs or configurations that permit suitable ingress and egress to the graft and/or crimping mechanisms may suitably be used. For example, a mandrel 40 with a donut-shaped bulbous portion 44 is depicted in a perspective view in FIG. 4. Mandrel 40 includes a tubular member 42 having an exterior surface 46. The donut 44 is disposed over the tubular member 42 as depicted in FIGS. 5 and 7 which are cross-sectional views of mandrel 40 taken along the 5-5 axis and the 7-7 axis, respectively.

Figure 7:
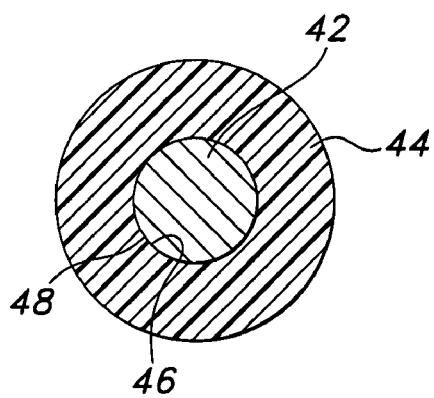
FIG. 7 is a cross-section view of the donut and the cylindrical member of FIG. 4 taken along the 7-7 axis.
Figure 6:
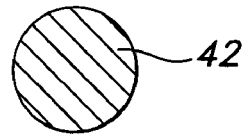
FIG. 6 is a cross-section view of the cylindrical member of FIG. 4 taken along the 6-6 axis.

As depicted in FIGS. 4-7, tubular member 42 is desirably a cylindrical tubular member as depicted in FIG. 7, but other shapes may suitably be used. The donut 44 is depicted generally as a spherical shape, but other shapes may suitably be used. For example, the donut 44 may be an oblong shape or shaped as a torus. As used herein, the term "donut" and its variants refer to a three dimensional shape having a bore or hole or orifice extending, either partially or totally, through the shape.

As depicted in FIG. 7, donut 44 includes an interior surface 48 to define an orifice or hole through, either totally or partially, the donut 44. The interior surface 48 is desirably mateable with the exterior surface 46 of tubular member 42. This permits the donut 44 to be disposed over tubular member 42, or the tubular member 42 to be along the donut 44.

The donut 44 may be made of resilient material, for example, silicone rubber, with the tubular member 42 being slidable through the orifice of donut 44. The use of resilient material is desirable because the donut 44 may be compressed away from a bulbous portion of a graft after crimping the graft and removing the tubular member 42. Alternatively, the donut 44 could be collapsible, disassembled, inflatable, deflateable and the life to permit ingress and egress of the tubular member 42 and to and from a bulbous graft portion.

The donut 44 and the tubular member 42 have crimping surfaces, (not shown), such as the previously described crimping surfaces. The graft 18 may be disposed over the mandrel 40 and ultrasonically crimped with a horn (not shown) with mateable crimping surfaces (not shown).

The graft 18 may be crimped, either totally or partially. For example, the tubular woven portion may be radially crimped, the bulbous woven portion may be radially crimped, or the tubular and the bulbous woven portions may be radially crimped.

In one aspect of the present invention a method of crimping a varied diameter graft is provided. The method includes the steps of (i) providing a flat-woven tubular graft 18 having an enlarged woven bulbous portion 20 disposed between flat-woven tubular ends, wherein the flat-woven diameter of the bulbous section is greater than the flat woven diameters of the tubular ends; (ii) providing a mandrel 14 shaped and sized to the woven bulbous section 20 and having a curved crimping surface 22; and (iii) positioning the curved crimping surface 22 within the bulbous woven section 20 so that the bulbous woven section 20 contours to the curved crimping surface 22.

The method of the present invention further includes the step of heating the bulbous woven portion 20 to set the shape of the bulbous woven portion 20. Alternatively, the method of the present invention may further include the step of applying heat and pressure to the bulbous woven portion 20 to set the shape of the bulbous woven portion 20. Desirably, the heating is caused by ultrasonic action.

The method of the present invention may further include the steps of (i) providing a horn 12 having a crimped surface 28 mateable to the crimped surface 22 of the mandrel 14; (ii) aligning the crimping surfaces 28 of the horn 12 over the bulbous woven section 20; (iii) securing the woven section 20 between the crimping surfaces 22, 28 of the horn 12 and the mandrel 14; and (iv) causing the woven portion to heat by ultrasonic action to heat set crimps thereat. The steps may be repeated until the graft is circumferentially crimped.

Further, the method of the present invention may include the steps of (i) providing a rotatable horn having a crimped surface mateable to the crimped surface of the rotatable mandrel made to rotate; (ii) aligning the crimping surfaces of the rotatable horn over the bulbous woven section; (iii) securing the woven section between the crimping surfaces of the rotatable horn and the rotatable mandrel; and (iv) causing the woven portion to heat by ultrasonic action to heat set crimps thereat.

In another aspect of the present invention, a method of crimping a varied diameter graft is provided. The method includes the steps of (i) providing a flat-woven tubular graft 18 having an enlarged woven bulbous portion 20 disposed between flat-woven tubular ends, wherein the flat-woven diameter of the bulbous section 20 is greater than the flat woven diameters of the tubular ends; (ii) providing a tubular cylindrical mandrel 42 having a diameter such that its exterior surface 46 is slidable engageable within the woven tubular ends; (iii) providing a bulbously shaped mandrel donut 44, the donut 44 being slidable over the cylindrical mandrel 42, the donut having a crimped exterior surface; (iv) aligning the donut 44 within the bulbous woven section 20 of the graft 18; (v) sliding the cylindrical mandrel 42 through the donut 44; (vi) crimping the graft 18 over the cylindrical mandrel 42 and bulbous donut 44; and (viii) removing the cylindrical mandrel 42 and the bulbous donut 44 from the graft 18. The removing step may further include the steps of (i) slidingly removing the cylindrical mandrel 42 from the graft 18 and the bulbous donut 44; and (ii) removing the donut 44 from the graft 18. The tubular mandrel 42 may include a crimping surface, and the flat-woven tubular ends may be crimped over the crimping surface of the mandrel 42. The removing step may further include the step of compressing the donut, collapsing the donut, disassembling the donut, and combinations thereof.

In another aspect of the present invention, a system 10 for crimping a varied diameter graft 18 is provided. The system 10 includes (i) a mandrel 14 having a bulbous portion 24, the bulbous portion 24 having a curved crimping surface 22; and (ii) a horn 12 having a curved crimped surface 28 aligningly engageable to the curved crimping surface 22 of the mandrel 14; and (iii) a source of ultrasonic energy.

In still another aspect of the present invention, a mandrel 14, 40 for crimping a varied diameter graft 18 is provided. The mandrel includes a mandrel 14, 42 with a bulbous portion 24, 44, the bulbous portion 24, 44 having a curved crimping surface 22.

In still further another aspect of the present invention, a mandrel 40 for crimping a varied diameter graft 18 is provided. The mandrel 40 includes (i) a tubular mandrel 42 having a diameter such that its exterior surface 46 is slidably engageable within a vascular tubular graft, wherein the exterior mandrel surface 46 has a crimping surface; and (ii) a bulbously shaped mandrel donut 44, wherein the donut 44 is slidable engageable over the tubular mandrel 42, the donut 44 having a curved exterior crimping surface. The donut 44 may be collapsible, expandable, inflatable, and combinations thereof. Further, the donut 44 may be made from a resilient material. Further, the donut 44 may be made from multiple parts and may be disassembleable.

The invention being thus described, it will now be evident to those skilled in the art that the same may be varied in many ways. Such variations are not to be regarded as a departure from the spirit and scope of the invention and all such modifications are intended to be included within the scope of the following claims.

What is claimed is:

1. A method of crimping a varied diameter graft comprising:
    (a) providing a flat-woven tubular graft having an enlarged woven bulbous portion disposed between flat-woven tubular ends, wherein the flat-woven diameter of said woven bulbous portion is greater than the flat-woven diameters of said tubular ends;
    (b) providing a mandrel shaped and sized to said woven bulbous portion and having a curved crimping surface;
    (c) positioning said curved crimping surface within said woven bulbous portion so that said woven bulbous portion contours to said curved crimping surface;
    (d) providing a horn having a crimped surface mateable to said crimped surface of said mandrel;
    (e) aligning said crimping surface of said horn over said woven bulbous portion;
    (f) securing said woven bulbous portion between said crimping surface of said horn and said crimping surface of said mandrel;
    (g) causing said woven bulbous portion to heat by ultrasonic action from said horn to heat set crimps thereat; and
    (h) rotating said graft around said mandrel and repeating steps (e) through (g) until the graft is circumferentially crimped.

2. The method of claim 1, further comprising heating said woven bulbous portion to set a bulbous shape of said woven bulbous portion.

3. The method of claim 2, further comprising applying pressure to said woven bulbous portion to set a bulbous shape of said woven bulbous portion.

4. The method of claim 2, wherein said heating is caused by ultrasonic action.

5. The method of claim 1, wherein step (f) further comprises applying pressure between said crimping surface of said horn and said crimping surface of said mandrel.

6. The method of claim 5, where said pressure is from about 10 psi to about 100 psi.

7. The method of claim 1, wherein said horn operates at a frequency of 20 kHz, 30 kHz, or 40 kHz.

8. A method of crimping a varied diameter graft comprising:
    (a) providing a flat-woven tubular graft having an enlarged woven bulbous portion disposed between flat-woven tubular ends, wherein the flat-woven diameter of said bulbous portion is greater than the flat-woven diameters of said tubular ends;
    (b) providing a rotatable mandrel shaped and sized to said woven bulbous portion and having a curved crimping surface;
    (c) positioning said curved crimping surface of said rotatable mandrel within said woven bulbous portion so that said woven bulbous portion contours to said curved crimping surface;
    (d) providing a rotatable horn having a crimped surface mateable to said crimped surface of said rotatable mandrel made to rotate;
    (e) aligning said crimping surface of said rotatable horn over said woven bulbous portion;
    (f) securing said woven bulbous portion between said crimping surface of said rotatable horn and said curved crimping surface of said rotatable mandrel; and
    (g) causing said woven bulbous portion to heat by ultrasonic action from said horn to heat set a bulbous shape of said woven bulbous portion and to heat set crimps thereat.

9. The method of claim 8, wherein step (f) further comprises applying an impingement force between said crimping surface of said rotatable horn and said crimping surface of said rotatable mandrel.

10. The method of claim 9, wherein the impingement force is at a pressure from about 10 psi to about 100 psi.

11. The method of claim 8, wherein said crimps are radially extending crimps.

12. The method of claim 8, wherein said rotatable horn operates at a frequency of 20 kHz, 30 kHz, or 40 kHz.

13. The method of claim 8, further comprising rotating said rotatable horn and said rotatable mandrel around the graft and repeating steps (e) through (g) until the graft is circumferentially crimped.

* * * * *